US00PP25815P2

(12) United States Plant Patent
Wood

(10) Patent No.: US PP25,815 P2
(45) Date of Patent: Aug. 18, 2015

(54) ***HYDRANGEA* PLANT NAMED 'SMHMSV'**

(50) Latin Name: *Hydrangea macrophylla*
Varietal Denomination: SMHMSV

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 132 days.

(21) Appl. No.: 13/987,988

(22) Filed: Sep. 20, 2013

(51) Int. Cl.
*A01H 5/02* (2006.01)

(52) U.S. Cl.
USPC ..... Plt./250

(58) Field of Classification Search
USPC ..... Plt./250
See application file for complete search history.

*Primary Examiner* — Anne Grunberg
(74) *Attorney, Agent, or Firm* — C. A. Whealy

(57) ABSTRACT

A new and distinct cultivar of *Hydrangea* plant named 'SMHMSV', characterized by its upright, outwardly spreading and mounded plant habit; strong and sturdy stems; light and dark green-colored variegated leaves; mophead and lacecap-type inflorescences with light pink-colored sterile flowers; and good winter hardiness.

2 Drawing Sheets

Botanical designation: *Hydrangea macrophylla.*
Cultivar denomination: 'SMHMSV'.

BACKGROUND OF THE INVENTION

The present invention relates to a new and distinct *Hydrangea* plant, botanically known as *Hydrangea macrophylla* and hereinafter referred to by the name 'SMHMSV'.

The new *Hydrangea* plant is a product of a planned breeding program conducted by the Inventor in Grand Haven, Mich. The objective of the breeding program was to develop new *Hydrangea* plants with reblooming habit, strong stems and attractive inflorescences.

The new *Hydrangea* plant is a naturally-occurring branch mutation of *Hydrangea macrophylla* 'Shugert', disclosed in U.S. Plant Pat. No. 21,591. The new *Hydrangea* plant was discovered and selected by the Inventor on a single plant of 'Shugert' from within a population of plants of 'Shugert' in 2007.

Asexual reproduction of the new *Hydrangea* plant by softwood cuttings in a controlled environment in Grand Haven, Mich. since June, 2007 has shown that the unique features of this new *Hydrangea* plant are stable and reproduced true to type in successive generations of asexual reproduction.

SUMMARY OF THE INVENTION

Plants of the new *Hydrangea* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'SMHMSV'. These characteristics in combination distinguish 'SMHMSV' as a new and distinct *Hydrangea* plant:

1. Upright, outwardly spreading and mounded plant habit.
2. Strong and sturdy stems.
3. Remontant flowering habit.

4. Light and dark green-colored variegated leaves.
5. Mophead and lacecap-type inflorescences with light pink-colored sterile flowers.
6. Good winter hardiness.

Plants of the new *Hydrangea* differ from plants of the female parent, 'Shugert', in the following characteristics:

1. Plants of the new *Hydrangea* have variegated leaves whereas plants of 'Shugert' have non-variegated leaves.
2. Plants of the new *Hydrangea* produce mophead and lacecap type inflorescences whereas plants of 'Shugert' only produce lacecap type inflorescences.

Plants of the new *Hydrangea* can be compared to plants of *Hydrangea macrophylla* 'Variegata', not patented. In side-by-side comparisons, plants of the new *Hydrangea* differed primarily from plants of 'Variegata' in the following characteristics:

1. Plants of the new *Hydrangea* had light and dark green-colored variegated leaves whereas plants of 'Variegata' had green and cream-colored variegated leaves.
2. Plants of the new *Hydrangea* produced mophead and lacecap type inflorescences whereas plants of 'Variegata' only produced lacecap type inflorescences.
3. Plants of the new *Hydrangea* rebloomed whereas plants of 'Variegata' did not rebloom.

Plants of the new *Hydrangea* can also be compared to plants of *Hydrangea macrophylla* 'Lemon Wave', not patented. In side-by-side comparisons, plants of the new *Hydrangea* differed primarily from plants of 'Lemon Wave' in the following characteristics:

1. Plants of the new *Hydrangea* had light and dark green-colored variegated leaves whereas plants of 'Lemon Wave' had green, yellow and golden yellow-colored variegated leaves.
2. Plants of the new *Hydrangea* produced mophead and lacecap type inflorescences whereas plants of 'Lemon Wave' only produced lacecap type inflorescences.

3. Plants of the new *Hydrangea* rebloomed whereas plants of 'Lemon Wave' did not rebloom.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a top perspective view of a typical plant of 'SMHMSV'.

The photograph on the second sheet is a close-up view of a typical flowering plant of 'SMHMSV'.

DETAILED BOTANICAL DESCRIPTION

Plants used for the aforementioned photographs and the following description were grown during the summer in three-gallon containers in an outdoor shadehouse in Grand Haven, Mich. and under cultural practices typical of commercial *Hydrangea* production. Plants of the new *Hydrangea* were three years old when the photographs and description were taken. In the following description, color references are made to The Royal Horticultural Society Colour Chart, 1995 Edition, except where general terms of ordinary dictionary significance are used.

Botanical description: *Hydrangea macrophylla* 'SMHMSV'.

Parentage: Naturally-occurring branch mutation of *Hydrangea macrophylla* 'Shugert', disclosed in U.S. Plant Pat. No. 21,591.

Propagation:

*Type cutting*.—By softwood cuttings.

*Time to initiate roots, summer*.—About ten days at temperatures about 24° C.

*Time to produce a rooted young plant, summer*.—About 40 days at temperatures about 24° C.

*Root description*.—Fine and medium in thickness, somewhat fibrous; white and brown in color.

*Rooting habit*.—Freely branching; dense.

Plant description:

*Plant form and growth habit*.—Perennial deciduous shrub; upright, outwardly spreading and mounded plant habit; inverted triangle; strong and sturdy lateral branches; freely branching habit with about 14 lateral branches developing per plant; vigorous growth habit.

*Plant height*.—About 35 cm.

*Plant diameter or area of spread*.—About 45 cm.

*Lateral branches*.—Length: About 25 cm. Diameter: About 4 mm. Internode length: About 3.2 cm. Texture: Smooth, glabrous. Strength: Strong, sturdy. Color, young: Close to 139D. Color, mature: Close to 138A.

Leaf description:

*Arrangement*.—Opposite, simple.

*Length*.—About 8.5 cm.

*Width*.—About 5.4 cm.

*Shape*.—Ovate.

*Apex*.—Acute to acuminate.

*Base*.—Cuneate.

*Margin*.—Crenate.

*Texture, upper and lower surfaces*.—Smooth, glabrous.

*Venation pattern*.—Pinnate.

*Color*.—Developing leaves, upper and lower surfaces: Close to 144A. Fully expanded leaves, upper surface: Central random sectors, close to 147A to 147B; surrounded by 145A to 145B and 144A to 144B; venation, close to 146B and 145A. Fully expanded leaves, lower surface: Central random sectors, close to 137D; surrounded by 145A; venation, close to 147B and 145A.

*Petioles*.—Length: About 1 cm. Diameter: About 2 mm. Texture, upper and lower surfaces: Smooth, glabrous. Color, upper and lower surfaces: Close to 145C.

Flower description:

*Flower type and habit*.—Single sterile and fertile flowers arranged on terminal mophead and lacecap-type cymes that are rounded; flowers face upright or outwardly.

*Fragrance*.—None detected.

*Natural flowering season*.—Plants flower throughout the summer in Grand Haven, Mich.; flowering remontant; flowers not persistent.

*Quantity of flowers*.—Freely flowering habit; about 64 fertile flowers and about 15 sterile flowers per inflorescence.

*Inflorescence height*.—About 4.5 cm.

*Inflorescence diameter*.—About 6 cm.

*Flower diameter, fertile flowers*.—About 6 mm.

*Flower depth (height), fertile flowers*.—About 3 mm.

*Flower diameter, sterile flowers*.—About 2.4 cm.

*Flower depth (height), sterile flowers*.—About 2 mm.

*Flower buds, fertile flowers*.—Length: About 6 mm. Diameter: About 1 mm. Shape: Obovate. Color: Close to 69B.

*Flower buds, sterile flowers*.—Length: About 4 mm. Diameter: About 2 mm. Shape: Spherical. Color: Close to 157B.

*Petals, fertile flowers only*.—Quantity per flower and arrangement: About 12 to 14 in about three whorls. Length: About 4 mm. Width: About 1.5 mm. Shape: Elliptic. Apex: Acute. Base: Cuneate. Margin: Entire. Texture, upper and lower surfaces: Smooth, glabrous. Color: When opening, upper surface: Close to 66D. When opening, lower surface: Close to 69A. Fully opened, upper and lower surfaces: Close to 69A.

*Sepals, fertile flowers*.—Quantity per flower and arrangement: Five in a single whorl. Length: About 1 mm. Width: About 1 mm. Shape: Subulate. Apex: Acute. Base: Cuneate. Margin: Entire. Texture, upper and lower surfaces: Smooth, glabrous. Color: When opening, upper and lower surfaces: Close to 62D. Fully opened, upper and lower surfaces: Close to 62D.

*Sepals, sterile flowers*.—Quantity per flower and arrangement: About five to eight in a single whorl. Length: About 1 cm. Width: About 7 mm. Shape: Obovate. Apex: Obtuse. Base: Attenuate. Margin: Entire. Texture, upper and lower surfaces: Smooth, glabrous. Color: When opening, upper surface: Close to 65B. When opening, lower surface: Close to 62D. Fully opened, upper surface: Close to 65D; color fading to close to 155A with development. Fully opened, lower surface: Close to 62D; color fading to close to 155A with development.

*Pedicels, fertile flowers*.—Angle: About 40° to 50° from inflorescence axis. Strength: Strong, sturdy. Length: About 5 mm. Diameter: About 1 mm. Texture: Smooth. Color: Close to 68D.

*Pedicels, sterile flowers*.—Angle: About 105° from inflorescence axis. Strength: Strong, sturdy. Length: About 1 cm. Diameter: About 2 mm. Texture: Smooth. Color: Close to 68D.

*Reproductive organs, fertile flowers*.—Stamens: Quantity per flower: About five. Filament length: About 3 mm. Filament color: Close to 74D. Anther shape: Round. Anther length: About 0.5 mm. Anther color: Close to 150D. Pollen amount: None observed. Pistils: Pistil quantity per flower: About three. Pistil length: About 2 mm. Stigma shape: Round. Stigma color: Close to 74B. Style length: About 1 mm. Style color: Close to 74C. Ovary color: Close to 75D.

*Reproductive organs, sterile flowers*.—Stamens: None observed on plants of the new *Hydrangea*. Pistils: Pistil quantity per flower: About three. Pistil length: About 1 mm. Stigma shape: Round. Stigma color: Close to 78D. Style length: About 1 mm. Style color: Close to 78D. Ovary color: Close to 75D.

*Seeds, fertile flowers only*.—Quantity per inflorescence: Numerous. Size: Less than 0.1 mm by less than 0.1 mm; dust-like. Color: Brown.

Disease & pest resistance: Plants of the new *Hydrangea* have not been observed to be resistant to pathogens and pests common to *Hydrangea* plants.

Temperature tolerance: Plants of the new *Hydrangea* have been shown to be tolerant to temperatures ranging from about −27° C. to about 37° C.

It is claimed:

1. A new and distinct *Hydrangea* plant named 'SMHMSV' as illustrated and described.

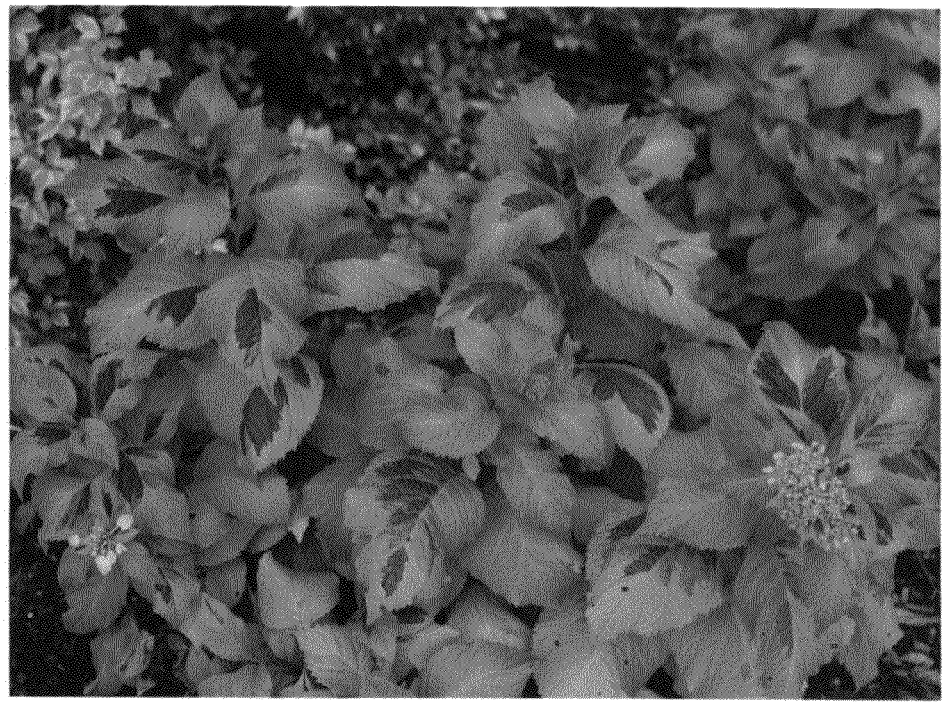

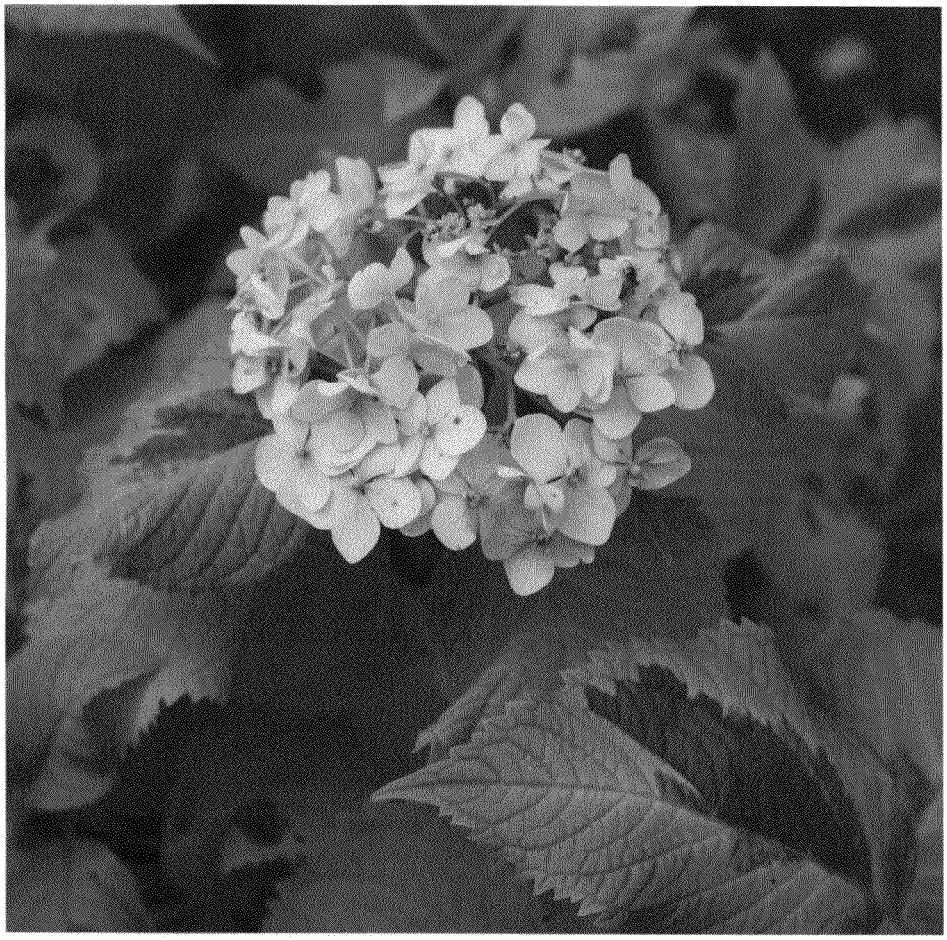

* * * * *